US009227905B2

(12) United States Patent
Klegraf et al.

(10) Patent No.: US 9,227,905 B2
(45) Date of Patent: Jan. 5, 2016

(54) PROCESS FOR THE PRODUCTION OF 4-CHLOROACETOACETYL CHLORIDE, 4-CHLOROACETOACETIC ACID ESTERS, AMIDES AND IMIDES (75) Inventors: Ellen Klegraf, Brig-Glis (CH); Miguel Angel Caraucan Davila, Birgisch (CH)

(73) Assignee: LONZA LTD., Visp (CH)

( * ) Notice: Subject to any disclaimer, the term of this patent is extended or adjusted under 35 U.S.C. 154(b) by 93 days.

(21) Appl. No.: 14/112,468

(22) PCT Filed: Apr. 25, 2012

(86) PCT No.: PCT/EP2012/057529
§ 371 (c)(1),
(2), (4) Date: Oct. 17, 2013

(87) PCT Pub. No.: WO2012/146604
PCT Pub. Date: Nov. 1, 2012

(65) Prior Publication Data
US 2014/0039217 A1   Feb. 6, 2014

Related U.S. Application Data (60) Provisional application No. 61/480,569, filed on Apr. 29, 2011.

(30) Foreign Application Priority Data
Apr. 29, 2011   (EP) .................................. 11003510

(51) Int. Cl.
C07C 51/58   (2006.01)
C07C 59/21   (2006.01)
C07C 67/14   (2006.01)
C07C 231/02   (2006.01)

(52) U.S. Cl.
CPC ................ *C07C 51/58* (2013.01); *C07C 59/21* (2013.01); *C07C 67/14* (2013.01); *C07C 231/02* (2013.01)

(58) Field of Classification Search
None
See application file for complete search history.

(56) References Cited

U.S. PATENT DOCUMENTS

| 3,701,803 A | 10/1972 | Boosen et al. |
| 3,950,412 A | 4/1976 | Boosen |
| 4,468,356 A | 8/1984 | Van Sickle et al. |
| 4,473,508 A | 9/1984 | Gross |

FOREIGN PATENT DOCUMENTS

| CN | 101121688 | 2/2008 |
| JP | 60 25951 | 2/1985 |
| JP | 60 25955 | 2/1985 |

(Continued)

OTHER PUBLICATIONS

English translation of Susumu et al. (JP 60 025955).*

(Continued)

*Primary Examiner* — Rosalynd Keys
*Assistant Examiner* — Jennifer C Sawyer
(74) *Attorney, Agent, or Firm* — Hoffmann & Baron, LLP (57) ABSTRACT The invention relates to process for the continuous production of 4-chloroacetoacetyl chloride, comprising the steps of (a) feeding diketene and chlorine into a thin film reactor and (b) reacting the diketene and chlorine to obtain 4-chloroacetoacetyl chloride. The invention also relates to a process for the production of 4-chloroacetoaceticacid ester, 4-chloroacetoaceticacid amide or 4-chloroacetoaceticacid imide from 4-chloroacetoacetyl chloride obtained according to the inventive process.

14 Claims, 3 Drawing Sheets

(56) References Cited

FOREIGN PATENT DOCUMENTS

| | | |
|---|---|---|
| JP | 62 053940 | 3/1987 |
| JP | 2003-113824 | 4/2003 |

OTHER PUBLICATIONS

English translation of Susumu et al. (JP 60025951).*
Sigma-Aldrich methanol specification comparison table.*
Elvers et al., Principles of chemical reaction engineering and plant design, Ullmann's Encyclopedia of Industrial Chemistry, vol. B4, (1992).
Pan et al., Synthesis of ethyl-(Z)-2-hydroxyimino-2-(2-aminothiazol-4-yl) acetate, Shandong Huagong, vol. 36(10), 4-6 (2007).
Steppan, et al., Wiped film reactor model for nylon 6,6 polymerization, Ind. Eng. Chem. Res., vol. 29, 2012-2020 (1990).

* cited by examiner

PROCESS FOR THE PRODUCTION OF 4-CHLOROACETOACETYL CHLORIDE, 4-CHLOROACETOACETIC ACID ESTERS, AMIDES AND IMIDES

This application is the U.S. National Phase of, and Applicants claim priority from International Patent Application Number PCT/EP2012/057529 filed 25 Apr. 2012, which claims priority from EP 11003510.2 filed 29 Apr. 2011 and U.S. Provisional Ser. No. 61/480,569 filed 29 Apr. 2011, each of which is incorporated herein by reference.

The invention relates to processes for the production of 4-chloroacetoacetyl chloride, 4-chloroacetoaceticacid esters, amides and imides.

BACKGROUND OF THE INVENTION

Methods for the production of 4-chloroacetoacetyl chloride 4-chloro-3-oxobutanoyl chloride) and esters obtained from 4-chloroacetoacetyl chloride are known in the art. In a specific process, the 4-chloroacetoacetyl chloride is obtained by reacting chlorine gas with diketene (4-methylideneoxetan-2-one).

The reaction takes place exothermally and therefore requires cooling. The reaction products are relatively sensitive to heat and the formation of undesired side products and decomposition is observed if temperature deviates locally or globally from a given range. For example, undesired reaction products may be regioisomers, such 2-chloroacetoacetyl chloride, or over-chlorinated products, such as di- or trihalogenated compounds, such as 2,4-dichloroacetoacetyl chloride or 2,2,4-trichloroacetoacetyl chloride. Thus, it is difficult to determine efficient production conditions by which a high yield is achieved.

JP 113 824 suggests a process in which diketene is dissolved in a solvent and reacted in a column reaction vessel with chlorine under cooling. The chlorine gas is fed into the column in a continuous current or counter-current manner. However, selectivities of less than 90% are achieved.

A solvent-free process is disclosed by U.S. Pat. No. 4,468, 356, according to which a diketene spray is continuously contacted with chlorine gas in a reaction zone at a temperature between 80° C. and 210° C. Subsequently, the intermediate product is subjected to an esterification reaction with ethanol. However, the overall yield is below 80% and thus relatively low, which is probably due to the exposure of the intermediate product to relatively high temperatures. Further, the reaction is carried out only with small amounts of starting compounds at a laboratory scale.

Reactions for the production of haloacetoacetic acids from diketene and chlorine on laboratory scale are disclosed in U.S. Pat. No. 3,950,412 and U.S. Pat. No. 3,701,803. In U.S. Pat. No. 4,473,508, the process of U.S. Pat. No. 3,701,803 is discussed. The inventors conclude that an upscale would not be possible because of problems associated with heat transfer. In order to provide an efficient reaction on increased scale, it is suggested to react a solution of diketene in an inert solvent with a solution of chlorine dissolved in an inert solvent in a tube reactor. According to Example 6, the acid chloride intermediate can be produced at a yield of 98%. However, the process is relatively inefficient, because both starting compounds are diluted in relatively large amounts of solvents. Thus, the overall reaction requires large amounts of solvent and consequently large reactors and equipment and more energy for cooling. When increasing the volume of the reactor, the yield dropped "drastically" and the selectivity was relatively low (U.S. Pat. No. 4,473,508, example 7). Thus it would be desirable to provide a more efficient process, which requires less solvent, is more selective and efficient on a large scale.

A laboratory process in order to produce ethyl-4-chloroacetoacetate from diketene and chlorine is disclosed by Pan et al., Shandong Huagong 2007, 36 (10) 4-6. In this process, it is suggested to use a relatively high concentration of diketene of about 24 to 28 weight-%. However, the yield of the ester is only about 80% and the reaction is carried out in a reaction flask on small scale, without any suggestion how to resolve the heat transfer problem on increased scale.

The processes known in the art are also problematic with respect to process safety. Especially when carried out in an industrial scale, the reaction requires high amounts of chlorine and diketene. These substances are highly reactive and hazardous when inhaled. When the reactor is damaged or when the process is disturbed and gets out of control, the reactants could harm the people in the environment and explode. Thus an industrial upscale, if at all, would only be possible under severe safety precautions.

PROBLEM UNDERLYING THE INVENTION

The problem underlying the invention is to provide a process for the production of 4-chloroacetoacetyl chloride and reaction products obtainable therefrom, which overcomes the above-mentioned problems. The process shall provide the reaction products at high yield and selectivity. The process shall be applicable on large-industrial scale use and as a continuous process. Specifically, the reaction efficiency shall be high and the consumption of solvents shall be low.

It is another problem underlying the invention to provide an industrial scale process, which is relatively safe and reduces the potential dangers associated with the handling of high amounts of chlorine and diketene.

DISCLOSURE OF THE INVENTION

Surprisingly, the problem underlying the invention is solved by processes according to the claims. Further inventive embodiments are disclosed throughout the description.

Subject of the invention is a process for the production of 4-chloroacetoacetyl chloride, comprising the steps of
(a) feeding diketene and chlorine into a thin film reactor and
(b) reacting the diketene and chlorine to obtain 4-chloroacetoacetyl chloride.

According to the invention, it was found that a highly efficient reaction between diketene and chlorine can be carried out in a thin film reactor. After feeding diketene and chlorine into the thin film reactor, they react in the thin film reactor. 4-chloroacetoacetyl chloride is formed as the reaction product and can be removed from the reactor.

In a preferred embodiment of the invention, in step (a) the diketene is fed into the reactor in the form of a mixture with an organic solvent. The mixture is preferably a solution of diketene in the organic solvent.

In principle, any organic solvent may be used, in which diketene is readily dissolved and which does not react with diketene or interfere with the reaction. Thus the solvent should be an inert solvent. In this respect, alcohols are not applicable, because they would react in an esterification reaction in the thin film reactor by acetoacetate formation. Preferred inert solvents are halogenated hydrocarbons, preferably halogenated alkanes, e.g. chloromethane, dichloromethane, trichloromethane (chloroform), tetrachloromethane, chloroethane, 1,2-dichlorethane, trichloroethane, tetrachloroethane, dichloropropane, 1-chloro-2-fluoroethane, 1,1-dichloroethane, 1,2-dichloroethane, methylchloroform, 1-chlorobutane, 2-chlorobutane, 1-bromobutane, ethyl bromide, 1-bromo-2-chloroethane, 1-bromo-2-fluoroethane, 1-iodobutane, bromochloromethane, dibromomethane, 1,1-dibromomethane, difluoroiodomethane, 1-bromopropane, bromochlorofluoromethane, 2-bromopropane, bromodichloromethane, bromofluoromethane, bromotrichloromethane, dibromodifluoromethane, pentachloromethane, 1,1,1,2-tetrachloroethane, fluoroiodomethane, iodomethane, diiodofluoromethane, 1,1,2,2-tetrachloromethane, 1,1,2-trichloroethane, 1-chloropropane, 1,2-dibromopropane, 1,2,3-trichloropropane, 1,1,1,2-tetrachloropropane, or mixtures thereof or mixtures comprising at least one thereof.

In a highly preferred embodiment of the invention, the solvent is dichloromethane. It is known in the art that dichloromethane is an efficient inert solvent for the reaction between diketene and chlorine.

According to the invention, it was found that the reaction can be carried out with high efficiency even when the diketene is provided in the organic solvent at relatively high concentrations. In a preferred embodiment of the invention, the concentration of diketene in the mixture is higher than 15% (w/w). More preferably, the concentration of diketene is higher than 20% or higher than 25% (w/w). The concentration of diketene could be up to 80% (w/w) or up to 50% (w/w). In preferred embodiments, the concentration of the diketene is between 15 and 80%, between 15 and 60% or between 20 and 50% (w/w), more preferably between 25 and 50% (w/w). The concentration of diketene could also be between 21% and 80%, preferably between 21 and 60% or between 21 and 50% (w/w). The relatively high concentration of diketene is advantageous, because the overall solvent consumption is low. Further, the volume of the reaction mixture in the thin flow reactor is kept relatively low. The contact area between the reactants is high and a good time-space yield can be obtained. Even further, the heat removal is more efficient if the volume is low and if thus the film thickness is also small. Thus the process is efficient regarding energy and costs, especially when carried out on industrial scale.

According to the invention, it is preferred that in step (a) the chlorine is fed into the reactor in the form of gaseous chlorine. When using gaseous chlorine, the total consumption of solvents is decreased even further. Thus, when using diketene at a relatively high concentration dissolved in an organic solvent, preferably dichloromethane, and using gaseous chlorine, the reaction is highly efficient for the reasons outlined above regarding high diketene concentrations. The reaction volume in the thin film reactor is relatively low and the time-space yield is increased, whereas heat transfer is facilitated. Further, the use of chlorine in gaseous form avoids a pre-dissolving step. This is advantageous, because chlorine is aggressive and complicated to handle on large-scale industrial process.

According to the invention, it is not necessary to dilute the chlorine with an inert gas. Thus in a preferred embodiment of the invention, no inert gas is introduced into the thin film reactor, and/or the chlorine is not mixed with an inert gas before or whilst being introduced into the thin film reactor. Preferably, only diketene, chlorine and the organic solvent are introduced into the thin film reactor. Thus the overall consumption of substances, and thus costs and energy, can be kept low.

The inventive reaction in step (a) is carried out in a thin film reactor. In such a thin film reactor, the reaction takes place on at least one reactor surface. Usually, thin film reactors allow a continuous renewal of the reaction surfaces. The thin films are created on the reaction surfaces by rotating the surfaces. The reactor is thus distinct from reactors, such as tube reactors, in which the reaction is carried out in a spatial liquid volume. The reactor comprises means for distributing the liquid reactants to the reaction surfaces. Further, the reactor should comprise cooling means. Preferably, the cooling means are a heat exchanger. In the inventive method, it is preferred that the heat, which is generated by the exothermic reaction, is continuously removed from the reactor. Thus, the reaction temperature can be maintained stable and relatively low, locally and globally. The thickness of the film is adapted to the cooling system and required heat dissipation. Typically, the average thickness of the film may be between 0.05 mm and 15 mm, more specifically between 0.1 and 5 mm.

In a highly preferred embodiment of the invention, the reactor is a wiped film reactor. A wiped film reactor comprises wiping means, for example blades, wipers or rolls. Typically, such rolls or wipers are pressed against the reactor walls by centrifugal forces. The wiping means are in contact with the films and moving, usually by rotation. By rotating the wiping means and thus the thin films, a film renewal and thorough and continuous mixing are achieved. The wiping means may be arranged in columns or rows. The wiping means are usually made from an inert material, such as PTFE (preferably available under the trademark Teflon from DuPont), metal alloys, preferably nickel alloys (preferably those available under the trademark Hastelloy from Haynes Int.), stainless steel, or graphite. Typically, the number of wiper elements is between 2 and 1000, more preferably between 10 and 1000 or between 50 and 500. For example, am industrial scale reactor may comprise 4 columns equipped with 40 rolls each. Wipers may be flat or wound, preferably spiral-wound.

Wiped film reactors are often used in the art for distillation of thermally labile compounds. However, the use of wiped film reactors for chemical reactions has also been described in the art. The use in a polymerisation reaction and adjustment of a reactor is described by Steppan et al. ("Wiped film reactor model for nylon 6,6 polymerisation", 1990, Ind. Eng. Chem. Res. 29, 2012-2020). The basic considerations disclosed therein are also useful for adjusting a wiped film reactor in the present inventive process for optimal yield. The reaction conditions are selected and adjusted In view of the specific reactor model, considering parameters such as number and type of wipers, liquid distribution system, temperature, reactor volume, pressure, rotor speed, desired film thickness etc.

The area of the wiped-film reactor is preferably between 0.5 and 30 $m^2$, preferably between 1 and 15 $m^2$. It is preferred that the area is at least 0.5, at least 1 or at least 2 $m^2$. The reactor speed may be between 10 and 2000 rpm, preferably between 20 and 1000 rpm.

In a preferred embodiment of the invention, the process is a continuous process. Preferably, the diketene is fed into the reactor at a rate of at least 10 kg/h. More preferably, the diketene is fed into the reactor at a rate of at least 20 kg/h, at least 30 kg/hour or at least 75 l/hour. The diketene may be fed into the reactor at a rate of between 10 and 500 kg/h, or between 75 to 250 kg/h. Thin film reactors are usually adjusted for continuous processes. The reactants are fed into the reactor at a constant speed, whereas the reaction product is withdrawn from the bottom of the reactor at a constant speed. It was found that the inventive reaction is efficient on relatively large scale, which is applicable for industrial production. Preferably, the chlorine gas is fed into the reactor at a rate of at least 10 kg/hour, 20 kg/h or 50 kg/h. The chlorine may be fed into the reactor at a rate of between 250 and 500 kg/h, or between 50 to 250 kg/h. The upscale processes can still provide the products at high yield and selectivity because of the low amounts of solvent and the high reaction efficiency and heat transfer efficiency in the specific reactor. This was surprising, because it was not expected that a scale-up of the reaction would be efficient with relatively low amounts of solvent and whilst obtaining high yields. Preferably, the volume of the thin film reactor is at least 50 l, at least 100 l or at least 500 l.

In an inventive upscale process, the turnover of the starting compounds and the reactor volume are relatively high. However, the reactants in the reactor are mostly present in the form of thin films, and thus the effective hold-up of reactants in the thin film reactor is significantly lower compared to a conventional batch or pipe reactor. In view of the potential dangers of the highly reactive and hazardous chlorine and diketene, the inventive process is thus generally safer. For example, when the reactor is damaged, or when the reaction gets out of control, relatively low amounts of chlorine and diketene could react in an uncontrolled manner or leak out of the reactor. The potential consequences would be less severe compared to a conventional reactor comprising a spatial batch volume with a high hold-up of chlorine and diketene. Thus the inventive process solves the problem of providing a safer process.

Moreover, it was found that the inventive reaction can be carried out with high efficiency on a large scale at relatively low temperatures. Diketene and 4-chloroacetoacetyl chloride are temperature-sensitive, such that the yield is decreased at high temperatures, especially when the residence time in the reactor is high. In a preferred embodiment of the invention, the reaction temperature is between −15° C. and 60° C. More preferably, the reaction temperature of the first reaction is maintained between −15° C. and 45° C. or between 0° C. and 30° C. Still preferably, the reaction temperature of the first reaction is maintained between 5° C. and 45° C. or between 5° C. and 30° C., or between 5° C. and 20° C. Preferably, the reaction temperature is below 60° C., below 40° C., below 30° C. or below 20° C. The reaction temperature is adjusted by cooling the reactor with cooling means, such as a heat exchanger. Preferably, the heat exchanger comprises a thermal fluid directly on the side of the surface which is not touched by the reaction mixture. The heat exchange can be carried out with good efficiency in a thin film reactor even on large scale. The average residence time of the diketene in the thin film reactor should be adjusted to be relatively low to avoid degradation and side reactions. The average residence time may be between 2 s and 500 s, or between 5 s and 250 s.

The reaction in the thin film reactor can be carried out at normal pressure, but also overpressure or sub-atmospheric or at light vacuum. The overall reaction can thus be carried out under mild conditions.

According to the invention, it was found that in view of low amounts of solvent and a high contact area in the reactor, even at low temperatures, the residence time of the reactants in the thin film reactor can be set relatively low whilst obtaining high yields. This was not expected, because at relatively low temperatures and on large-scale, the residence time is in principle increased. However, the overall set-up, with thin film formation, preferably supported by wiping, reduces the residence time.

As outlined above, the total amount of solvent used in the inventive process can be kept relatively low. The consumption of solvent can be reduced even further when the solvent is recycled. More preferably, the solvent is also reused in the process. In a preferred embodiment of the invention, the solvent is recycled and reused. The recycling may comprise any appropriate methods, such as distillation, liquid-liquid extraction, reactive extraction, membrane separation technology, chromatography or crystallisation of the solvent, or a combination of these methods, after the esterification or amidation reaction. Subsequently, the purified solvent is re-introduction into the process, preferably after mixing it with diketene in the reactant stream.

In a preferred embodiment of the invention, the solvent is dichloromethane having a purity of at least 98 weight-%. Preferably, the content of chloride, water and/or alcohol is low.

Another subject of the invention is a process for the production of a 4-chloroacetoaceticacid ester, a 4-chloroacetoaceticacid amide or a 4-chloroacetoaceticacid imide, comprising the steps
  (c) transferring 4-chloroacetoacetyl chloride obtained according to a process of the invention into a second reactor and
  (d) reacting the 4-chloroacetoacetyl chloride with an alcohol or amine to obtain the 4-chloroacetoaceticacid ester, 4-chloroacetoaceticacid amide or a 4-chloroacetoaceticacid imide.

Hence the reaction product of the initial reaction of diketene and chlorine can be reacted further in a second reaction. Preferably, the first and second reactions are part of one single continuous process. In such a continuous process, the 4-chloroacetoacetyl chloride built from the first reaction is withdrawn from the first reactor, which is the thin film reactor, and transferred directly into the second reactor.

In the second reactor, the esterification, amidation or imidation reaction is carried out. The reactor may be any type of reactor, which is appropriate for these reactions. For example, the reactor may be or may comprise a vessel, tube or column. The first and second reactors are connected by connection means, such as a tube, pipe or hose. Thus, the overall process can be carried out in an efficient manner without intermediate purification or isolation of the 4-chloroacetoacetyl chloride. However, the reaction could also be carried out after intermediate isolation of the 4-chloroacetoacetyl chloride.

The esterification, amidation or imidation reaction is a typical reaction of an acid chloride with an alcohol or amine.

In a preferred embodiment, the alcohol is an alkyl alcohol, i.e. an alkanol, or an aryl alcohol, such as a phenol. For example, the alcohol may be selected from the group of methanol, ethanol, isopropanol, n-butanol, tert-butanol and phenol. In preferred embodiments, the alcohol is methanol, ethanol or phenol. In order to obtain an amide, a primary or secondary amine is used, preferably an alkyl amine, such as a cyclic secondary alkyl amine, or an aryl amine, such as aniline. The aryl group of aniline may be substituted. The alkyl groups of the alcohol or amine may have between one and 10 carbon atoms, preferably between 1 and 4 carbon atoms.

During the second reaction, HCl is formed in virtually stoichiometric amounts. The amount of HCl product emerging during the process is virtually equimolar to the product (and side products). Preferably, the gaseous HCl is removed from the offgas by neutralization, for example with a basic scrubber system. However, usually residual amounts of HCl are dissolved in the solvents. Before reusing the solvents, the remaining amount of HCl has to be neutralized, e.g. by extraction with aqueous basic solution.

The reaction conditions, such as temperature and pressure, are adapted to obtain a high yield whilst consuming relatively low amounts of energy.

In a preferred embodiment of the invention, the reaction temperature in step (d) is between 0° C. and 80° C., or preferably between 20° C. ad 60° C. The reaction may be carried out at normal pressure, overpressure or negative pressure.

Preferably, the dichloromethane solvent is distilled and/or recycled after the second reaction in step (d). In or before the recycling step, the HCl should be removed from the solvent, preferably by neutralization. The solvent may be purified by known means, for example using a dewatering column, molecular sieves, membrane separation technology, liquid-liquid extraction, reactive extraction, chromatography and/or crystallisation, or a combination of these methods.

In a preferred embodiment of the invention, the yield of the 4-chloroacetoaceticacid ester, 4-chloroacetoaceticacid amide or 4-chloroacetoaceticacid imide is at least 90%, based on the total amount of ketene provided in step (a). More preferably, the yield is above 92% or above 95%. Preferably, the yield of 4-chloroacetoacetate chloride obtained in the first reaction step is more than 90%, preferably more than 95% or more than 98%. Preferably, the conversion of chlorine is at least 95%, more preferably at least 98% or at least 99.5%.

Figure 1:
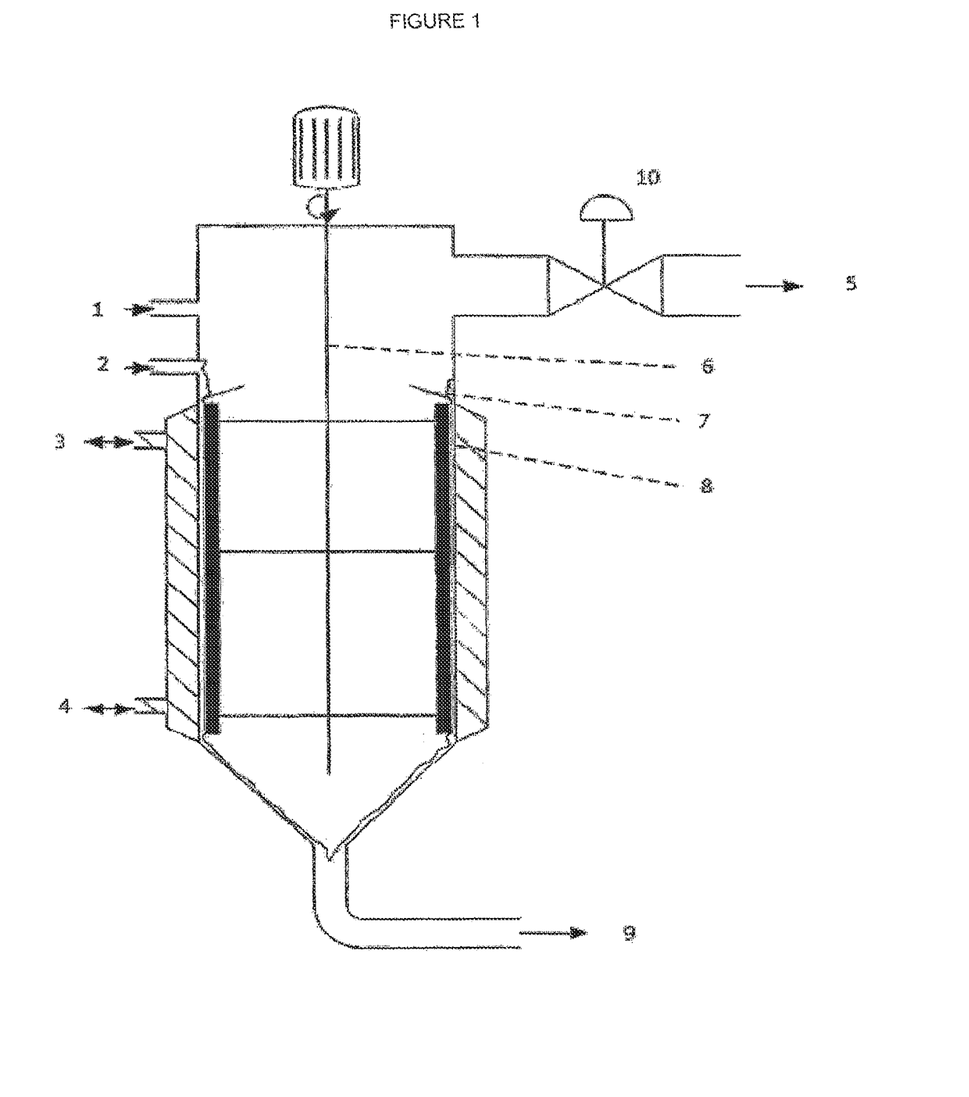
FIG. 1 shows schematically and in exemplified form a wiped film reactor applicable in the inventive process.
Figure 2:
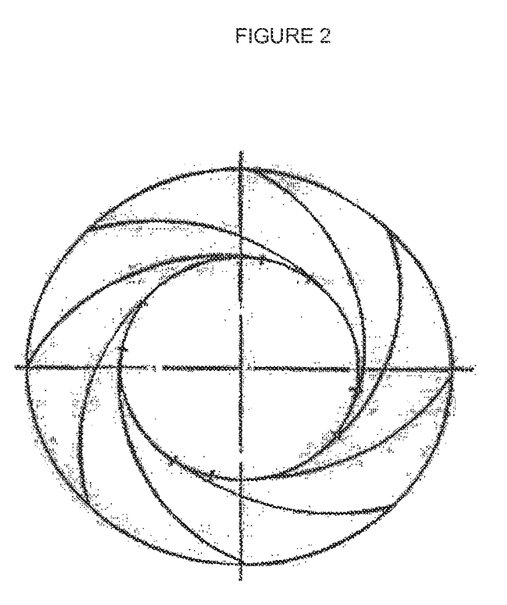
FIG. 2 shows schematically and in exemplified form the top view of a possible layout of wipers inside a thin film chlorination reactor.

A wiped film reactor for use in the first reaction of the invention is shown in FIG. 1. The reactor comprises means (1) and (2) for feeding the diketene and chlorine. The reactor comprises means (3) and (4) for supplying heat exchanging fluid into the heat exchanging means. The product is eluted through means (9), whereas vapors and/or gas can be let out through means (5), which may comprise a valve (10). The reactor comprises a rotor axis (6), around which a circular movement occurs. The reaction mixture is fed to the reactor in a manner to flow down on the outer portions of the reactor where it is mixed and distributed. The reactor comprises means for distributing the liquid (7) and wipers (8), on which the thin film is formed. A top view of a thin film reactor with spiral-wound wiper plates is shown in FIG. 2.

Figure 3:
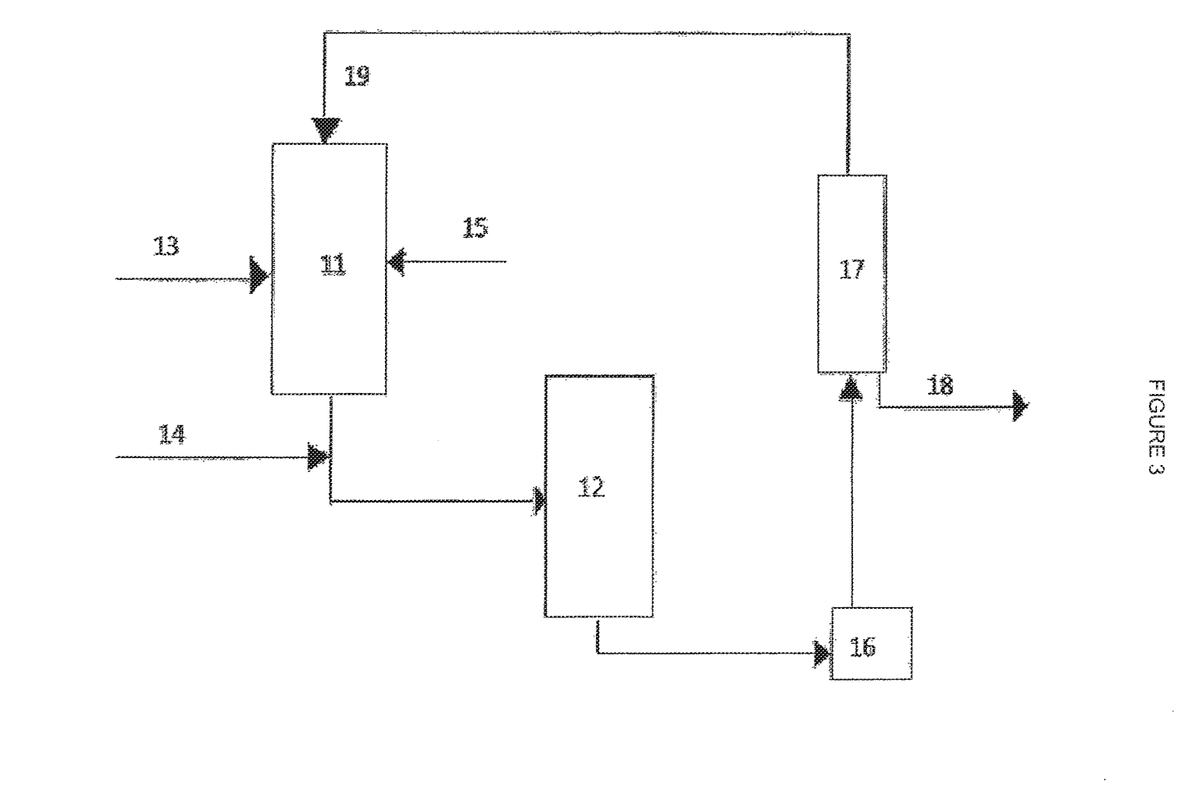
FIG. 3 shows schematically and in exemplified form a set-up for an inventive continuous process for the production of 4-chloroacetoacetate from diketene and gaseous chlorine.

A typical arrangement of the inventive process is illustrated by FIG. 3. Shown is an exemplified pathway with thin film reactor for carrying out the conversion of diketene and gaseous chlorine, whereas the diketene is dissolved in an organic solvent, and transfers to a second reactor unit for the production of 4-chloroacetoaceticacid ester, 4-chloroacetoaceticacid amide or a 4-chloroacetoaceticacid imide. The gaseous chlorine and diketene solution are fed into the thin film reactor (11) through inlets (13) for diketene solution and (15) for chlorine. The 4-chloroacetoacetyl chloride intermediate is eluted from reactor (11) and combined with the alcohol or amine reagent which is fed into the reaction stream through inlet (14). The reaction stream enters the reactor (12). The crude reaction product is withdrawn to obtain a crude product (16), which is purified by distillation means (17) and isolated through outlet (18). The solvent may be recycled through recycling means (18) and returned back to the reaction of chlorination through connection (19). The reactors (11), (12) and means (16), (17) are connected by connection means, such as tubes or hoses. The dimensions, connections and positions of inlets and outlets are only shown schematically and not to be understood as limiting.

The inventive process solves the problems underlying the invention. The invention provides an efficient process for reacting diketene with chlorine to obtain 4-chloroacetoacetyl chloride and reaction products obtainable therefrom. The reactions can be carried out with high selectivity and yield. Low amounts of solvent are used, which makes the processes more efficient. The process is efficient at low temperatures. A scale-up is possible whilst maintaining a high yield. Overall, the reactants in the reactor have a low residence time, high throughput and high time-space yield, combined with good heat removal in the first reactor.

It was further observed that uniform heat removal is possible in the thin film reactor, such that local overheating is not observed. Local overheating can lead to partial decomposition of reactants or products. Further, the inventive chlorination reaction provides high selectivity and only minor amounts of over-chlorinated products, which could result in undesired side products. Dissolving of the chlorine in solvent is not necessary, which renders the process more efficient and easier to handle. The solvent can be recycled and re-introduced into the process.

EXAMPLES

Example 1

Production of 4-CAAMe on Pilot Scale

The reaction of chlorination of diketene takes continuously place on pilot scale in a wiped-film-reactor (chlorination reactor) with 1.5 m$^2$ area. The reactor has 20 wipers. The wipers are aligned in five rows along the reactor. Each row has four wipers separated 90° from each other. The wipers of one row are 25° staggered in relationship to the position of the wipers corresponding to the nearby row. The wipers are assembled as spiral-wound Teflon plates. FIG. 2 shows schematically how the wipers are mounted inside the reactor. The reactor-rotor speed was varied between 80 rpm and 500 rpm.

The reactants chloride gas ($Cl_2$) and diketene are introduced at the top of the reactor. The solvent in this reaction is dichloromethane ($MeCl_2$). Before diketene is fed into the reactor, it is diluted in $MeCl_2$. The mixture of diketene and $MeCl_2$ is prepared inline using a static mixer. In order to remove the heat produced by the reaction between $Cl_2$ and diketene, the reactor is intensively cooled with a closed cooling system. During the reaction of $Cl_2$ with diketene, the intermediate product 4-chloro-3-oxobutanoyl chloride (4-CAAC) is produced.

4-CAAMe is subsequently produced by adding methanol (MeOH) to the reacting mixture leaving the chlorination reactor. MeOH is directly added into the pipeline which connects the chlorination reactor with the esterification reactor. During the reaction of esterification one equivalent of HCl is formed. The gases of the reaction—mainly HCl—are sent to a scrubber system operated with an aqueous solution of NaOH. The liquid mixture after the esterification reactor is sent to the distilling purification steps. $MeCl_2$ is recycled to the reaction after its corresponding purification.

In a typical production campaign of 4-CAAMe, 27 to 30 l/h diketene together with 45 l/h $MeCl_2$ and 25 kg/h of $Cl_2$ gas are continuously fed into the chlorination reactor. The speed of the reactor-rotor was controlled between 200 and 350 rpm. In order to avoid the decomposition of diketene in the store tank, the temperature in the diketene tank is kept at 9 to 14° C. $Cl_2$ is normally dosed in a light excess (1 to 8%) with respect to diketene.

The temperature of the mixture leaving the chlorination reactor is 12° C. to 15° C. The pressure in the reactor is kept under light vacuum of about −0.1 to −8 mbarg. The esterification of the mixture is carried out adding 22-23 l/h MeOH. During the reaction of esterification, the temperature of the mixture increases to 30-44° C. This material flows to a column filled with ceramic random packing, where the esterification is completed. The reaction of esterification generates one equivalent of HCl. The HCl is conduced to a scrubber system operated with NaOH. The liquid phase of the esterification column overflows through a siphon in the flash distillation of $MeCl_2$. The $MeCl_2$ obtained from the flash distillation is collected and sent to a recovering process designed to recycle this $MeCl_2$ to the reaction.

The conversion of $Cl_2$ in the chlorination reaction is estimated to be 100%. The selectivity to 4-CAAC is 95%, the selectivity to 2,4-CAAC is 2%, the selectivity to other Cl-compounds is estimated to be 3%.

Example 2

Production of 4-CAAEt on Pilot Scale

The production of 4-CAAEt on pilot scale is carried out using the same setup as the production of 4-CAAMe described in the example 1.

The reactants chloride gas ($Cl_2$) and diketene are introduced at the top of the reactor. The solvent in this reaction is dichloromethane ($MeCl_2$). Before diketene is fed into the reactor, it is diluted in $MeCl_2$. The mixture diketene and $MeCl_2$ is prepared inline using a static mixer. In order to remove the heat produced by the reaction between $Cl_2$ and diketene, the reactor is intensively cooled with a closed cooling system. During the reaction of $Cl_2$ with diketene, the intermediate product 4-chloro-3-oxobutanoyl chloride (4-CAAC) is formed.

4-CAAEt is produced by adding ethanol (EtOH) to the reacting mixture leaving the chlorination reactor. EtOH is directly added in the pipeline discharging in the esterification reactor. During the reaction of esterification 4-CAAEt and HCl are formed. The gases of the reaction—mainly HCl—are sent to a scrubber system operated with an aqueous solution of NaOH. The liquid mixture after the esterification reactor is sent to the distilling purification steps. $MeCl_2$ is recycled to the reaction after its corresponding purification.

In a typical production campaign of 4-CAAEt, 39 l/h diketene together with 70 l/h MeCl2 and 31 kg/h of $Cl_2$ gas are continuously fed into the chlorination reactor. The speed of the reactor-rotor was controlled between 200 and 350 rpm. In order to avoid the decomposition of diketene in the store tank, the temperature in tank is kept at 9 to 14° C. $Cl_2$ is normally dosed in a light excess (1 to 8%) with respect to diketene.

The temperature of the mixture leaving the chlorination reactor is 17° C. to 19° C. The pressure in the reactor is kept under light vacuum of about −0.1 to −8 mbarg. The esterification of the mixture is carried out adding 27 l/h EtOH. During the reaction of esterification, the temperature of the mixture increases to 40-53° C. This material flows to a column filled with ceramic random packing, where the reaction of esterification is completed. The esterification reaction generates one equivalent of HCl. The HCl is conducted to a scrubber system operated with NaOH. The liquid phase of the esterification column overflows through a siphon in the flash distillation of $MeCl_2$.

The conversion of $Cl_2$ in the chlorination reaction is estimated to be 100%. The selectivity to 4-CAAC is 95%, the selectivity to 2,4-CAAC is 2%, the selectivity to other Cl-compounds is estimated to 3%.

Example 3

Production of 4-CAAEt on Industrial Scale

The reaction of chlorination of diketene takes continuously place on industrial scale in a wiped-film-reactor (chlorination reactor) with 4 $m^2$ area. The reactor has 160 rolls as wiper elements. The wiper elements are assembled as cylindrical graphite rolls. The centrifugal force presses the rolls to the reactor wall. The rolls are aligned in four vertical columns along the reactor circumference. Each column has 40 rolls. The reactor-rotor speed was varied between 40 rpm and 200 rpm.

The reactants chloride gas ($Cl_2$) and diketene are introduced at the top of the reactor. The solvent in this reaction is dichloromethane ($MeCl_2$). Before diketene is fed into the reactor, it is diluted in $MeCl_2$. The mixture diketene and $MeCl_2$ is prepared inline using a static mixer. In order to remove the heat produced by the reaction between $Cl_2$ and diketene, the reactor is intensively cooled with a closed cooling system. During the reaction of $Cl_2$ with diketene, the intermediate product 4-chloro-3-oxobutanoyl chloride (4-CAAC) is produced.

4-CAAEt is synthesized by adding ethanol (EtOH) to the reacting mixture leaving the chlorination reactor. EtOH is directly added in the pipeline connecting the chlorination reactor to the esterification reactor. During the reaction of esterification 4-CAAEt and HCl are formed. The gases of the reaction—mainly HCl—are sent to a scrubber system operated with an aqueous solution of NaOH. The liquid mixture after the esterification reactor is sent to the distilling purification steps. MeCl2 is recycled to the reaction after its corresponding purification.

In a typical production campaign of 4-CAAEt, 75 to 150 kg/h diketene together with 150 to 600 kg/h $MeCl_2$ and 62 to 135 kg/h of $Cl_2$ gas are continuously fed into the chlorination reactor. The speed of the reactor-rotor is controlled between 70 and 120 rpm. In order to avoid the decomposition of diketene in the store tank, the temperature in tank is kept at 9 to 14° C. $Cl_2$ is normally dosed in a light excess (1 to 6%) with respect to diketene.

The temperature of the mixture leaving the chlorination reactor is −5° C. to 30° C. The pressure in the reactor is kept under light vacuum of about −0.1 to −10 mbarg. The esterification of the mixture is carried out adding 40 to 80 kg/h EtOH. During the esterification reaction the temperature of the mixture increases to 20-55° C.

This material flows to a column filled with ceramic random packing, where the esterification is completed. This reaction generates one equivalent of HCl as side product. The HCl is conducted to a scrubber system operated with NaOH. The liquid phase of the esterification column overflows through a siphon in the flash distillation of $MeCl_2$.

The conversion of $Cl_2$ in the chlorination reaction is estimated to be 100%. The selectivity to 4-CAAC is 95%, the selectivity to 2,4-CAAC is 2%, the selectivity to other Cl-compounds is estimated to be 3%.

The experiments show that the inventive process can be scaled up and carried out in an industrial scale without significant problems whilst maintaining a high yield and selectivity.

The invention claimed is:

1. A process for the production of 4-chloroacetoacetyl chloride, comprising the steps of
    (a) feeding diketene and chlorine into a wiped film reactor and
    (b) reacting the diketene and chlorine to obtain 4-chloroacetoacetyl chloride,
wherein in step (a) the diketene is fed into the reactor in the form of a mixture with an organic solvent, wherein the concentration of the diketene in the mixture is higher than 15% (w/w), wherein in step (a) the chlorine is fed into the reactor in the form of gaseous chlorine, wherein the chlorine is not diluted with an inert gas, and wherein the process is a continuous process, wherein the diketene is fed into the reactor at a rate of at least 10 kg/h.

2. The process of claim 1, wherein the solvent is a halogenated alkane.

3. The process of claim 1, wherein the diketene is fed into the reactor at a rate of at least 75 kg/h.

4. The process of claim 1, wherein the reaction temperature is between −15° C. and 60° C.

5. The process of claim 1, wherein the solvent is recycled and reused in the process.

6. The process of claim 1, wherein the solvent has a purity of at least 98 weight %.

7. A process for the production of a 4-chloroacetoaceticacid ester, a 4-chloroacetoaceticacid amide or a 4-chloroacetoaceticacid imide, comprising the steps
  (c) producing 4-chloroacetoacetyl chloride according to a process of any of the preceding claims, transferring it into a second reactor, and
  (d) reacting the 4-chloroacetoacetyl chloride with an alcohol or amine to obtain the 4-chloroacetoaceticacid ester, 4-chloroacetoaceticacid amide or a 4-chloroacetoaceticacid imide.

8. The process of claim 7, wherein the alcohol is an alkanol.

9. The process of claim 7, wherein the reaction temperature in step (d) is between 0° C. and 80° C.

10. The process of claim 8, wherein the reaction temperature in step (d) is between 0° C. and 80° C.

11. The process of claim 7, wherein the yield of the 4-chloroacetoaceticacid ester, 4-chloroacetoaceticacid amide or 4-chloroacetoaceticacid imide is at least 90%, based on the total amount of ketene provided in step (a).

12. The process of claim 8, wherein the yield of the 4-chloroacetoaceticacid ester, 4-chloroacetoaceticacid amide or 4-chloroacetoaceticacid imide is at least 90%, based on the total amount of ketene provided in step (a).

13. The process of claim 2 wherein said halogenated alkane is selected from chloromethane, dichloromethane, trichloromethane (chloroform), tetrachloromethane, chloroethane, 1,2-dichlorethane, trichloroethane, tetrachloroethane, dichloropropane, 1-chloro-2-fluoroethane, 1,1-dichloroethane, 1,2-dichloroethane, methylchloroform, 1-chlorobutane, 2-chlorobutane, 1-bromobutane, ethyl bromide, 1-bromo-2-chloroethane, 1-bromo-2-fluoroethane, 1-iodobutane, bromochloromethane, dibromomethane, 1,1-dibromomethane, difluoroiodomethane, 1-bromopropane, bromochlorofluoromethane, 2-bromopropane, bromodichloromethane, bromofluoromethane, bromotrichloromethane, dibromodifluoromethane, pentachloromethane, 1,1,1,2-tetrachloroethane, fluoroiodomethane, iodomethane, diiodofluoromethane, 1,1,2,2-tetrachloromethane, 1,1,2-trichloroethane, 1-chloropropane, 1,2-dibromopropane, 1,2,3-trichloropropane, 1,1,1,2-tetrachloropropane and mixtures thereof or mixtures comprising at least one thereof.

14. The process of claim 8, wherein said alkanol is selected from the group of methanol, ethanol, isopropanol, tert-butanol or phenol.

* * * * *